United States Patent
Schoepgens et al.

(10) Patent No.: US 8,801,805 B2
(45) Date of Patent: Aug. 12, 2014

(54) AGENT COMPRISING HYDROGEN PEROXIDE HAVING IMPROVED VISCOSITY ADJUSTMENT

(71) Applicant: Henkel AG & Co. KGaA, Duesseldorf (DE)

(72) Inventors: Juergen Schoepgens, Schwalmtal (DE); Frank Janssen, Cologne (DE); Armin Wadle, Erkrath (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/181,470

(22) Filed: Feb. 14, 2014

(65) Prior Publication Data

US 2014/0158150 A1    Jun. 12, 2014

Related U.S. Application Data

(63) Continuation of application No. PCT/EP2012/063564, filed on Jul. 11, 2012.

(30) Foreign Application Priority Data

| Aug. 26, 2011 | (DE) | .......................... | 10 2011 081 607 |
| Aug. 26, 2011 | (DE) | .......................... | 10 2011 081 608 |
| Aug. 26, 2011 | (DE) | .......................... | 10 2011 081 610 |
| Aug. 26, 2011 | (DE) | .......................... | 10 2011 081 611 |
| Aug. 26, 2011 | (DE) | .......................... | 10 2011 081 612 |

(51) Int. Cl.

| *A61Q 5/08* | (2006.01) |
| *A61K 8/87* | (2006.01) |
| *A61K 8/81* | (2006.01) |
| *A61K 8/22* | (2006.01) |
| *A45D 19/00* | (2006.01) |

(52) U.S. Cl.
CPC ............... *A61K 8/87* (2013.01); *A61K 8/8147* (2013.01); *A61K 8/22* (2013.01); *A61Q 5/08* (2013.01); *A45D 19/00* (2013.01)
USPC ........................... 8/101; 8/552; 8/558; 8/580

(58) Field of Classification Search
USPC ....................................... 8/101, 552, 558, 580
See application file for complete search history.

(56) References Cited

U.S. PATENT DOCUMENTS

| 2004/0034946 A1 | 2/2004 | Legrand et al. | |
| 2004/0060126 A1* | 4/2004 | Cottard et al. | .................... 8/405 |
| 2009/0081137 A1 | 3/2009 | Nguyen Kim et al. | |
| 2012/0312318 A1 | 12/2012 | Krippahl et al. | |

FOREIGN PATENT DOCUMENTS

| EP | 0978522 A1 | 2/2000 |
| EP | 2338470 A1 | 6/2011 |
| WO | 02/068488 A2 | 9/2002 |

OTHER PUBLICATIONS

PCT International Search Report (PCT/EP2012/063564) dated Jan. 14, 2013.
Anonymous, "Luvigel STAR—Non-ionic, electrolyte tolerant, polyurethane-based associative rheology modifier for personal care applications like skin & sun care, decorative cosmetic or cleansing products", http://www.univarusa.com/vwr-inc/tools.nsf/0/6589FB4296753E54882575F5004FDD57/$file/Luvigel%2OSTAR.pdf (retrieved Nov. 15, 2010), pp. 1-18, Apr. 1, 2009.

* cited by examiner

*Primary Examiner* — Eisa Elhilo
(74) *Attorney, Agent, or Firm* — David K. Benson

(57) ABSTRACT

An agent includes in a cosmetically suitable carrier at least hydrogen peroxide, at least one homo- or copolymer of acrylic acid and/or methacrylic acid and at least one polyurethane, wherein the polyurethane is a polycondensation product of polyethylene glycol(s), diisocyanate(s) and optionally ethoxylated fatty alcohol(s).

10 Claims, No Drawings

AGENT COMPRISING HYDROGEN PEROXIDE HAVING IMPROVED VISCOSITY ADJUSTMENT

FIELD OF THE INVENTION

The present invention generally relates to a hydrogen peroxide-containing agent including a combination of at least two specific polymers, for use in oxidative color modifying preparations for keratinic fibers, in particular human hair, which combination has an improved viscosity. Said improvement in viscosity is achieved by the interaction of an anionic polymeric thickener in conjunction with a specific polyurethane

BACKGROUND OF THE INVENTION

Modifying the shape and color of hair is an important area of modern cosmetics. In this way, the hair's appearance can be adapted both to current fashion trends and to a person's individual wishes. Apart from the desired coloring and shaping performance, these agents should cause the least possible damage to the hair and should preferably even have additional conditioning properties.

Depending on the requirements placed on the dyed color, a person skilled in the art is aware of various coloring systems for providing color-modifying cosmetics, in particular for the skin or keratin-containing fibers such as for example human hair. "Oxidation coloring agents", as they are known, are used for permanent, high intensity coloring results with corresponding fastness characteristics. Such coloring agents conventionally include oxidation dye precursors, known as "developer components" and "coupler components" which, under the influence of oxidizing agents or atmospheric oxygen, react with one another to form the actual dyes. Two-part coloring agents are accordingly for the most part used, from which the mixtures for use are produced only immediately prior to use from a color modifying preparation and an oxidizing agent preparation. Oxidation coloring agents are distinguished by excellent, long-lasting coloring results.

Lightening agents or blonding agents are also conventionally produced immediately prior to use from a hydrogen peroxide-containing oxidation preparation and a blonding powder and/or an alkalizing preparation.

For the purposes of the present application, oxidation coloring agents, lightening agents and blonding agents for keratinic fibers are referred to as color modifying preparations.

In order to achieve optimum coloring or lightening performance, oxidative color modifying preparations generally require an alkaline pH value, in particular between pH 9.0 and pH 11.5. The period of use for attractive coloring results is furthermore conventionally between 10 and 45 min and conventionally between 15 and 60 min for lightening results.

It is therefore necessary for the ready-to-use color modifying preparations to be formulated and packaged such that the color modifying preparation may, on the one hand, readily be distributed onto the keratinic fibers to be treated, while, on the other hand, remaining in the fibers to be treated during the time of use. It is advantageous to this end for the color modifying preparation to have a specific viscosity which, while permitting application of the agent, also retains the agent at the place of use. On the other hand, for the purpose of using the color modifying preparation, it is desirable for it to be possible to produce the preparation by simply mixing the starting preparations (coloring preparation and oxidizing agent preparation for oxidation coloring agents or oxidizing agent preparation and blonding powder and/or alkalizing preparation for lightening and blonding agents) and furthermore for the preparation to be easy to dispense from the mixing vessel and to apply onto the fibers to be treated.

The viscosity required for this purpose may be established by polymeric thickeners in the ready-to-use color modifying preparation, wherein said thickener may be present both in the coloring preparation or alkalizing preparation or in the oxidizing agent preparation.

In order to enable effective mixing, it is advantageous for the coloring preparation or alkalizing preparation and the oxidizing agent preparation to have good fluidity and for the elevated viscosity of the mixture for use only to be established once the two components have been mixed. One option for achieving this aim is to use polymeric thickeners having thickening properties which vary with pH value. A color modifying preparation usually has an alkaline pH value to stabilize oxidation dye precursors and the oxidizing agent preparation has an acidic pH value to stabilize the oxidizing agent, while the mixture for use is intended to have an alkaline pH value. If the polymeric thickener is present in the acidic oxidizing agent preparation, an anionic polymeric thickener which gives rise to a distinct increase in viscosity at an alkaline pH value is thus preferred.

Homo- or copolymers of acrylic acid or methacrylic acid are particularly suitable as such anionic, polymeric thickeners. Relatively large quantities, conventionally between 2.5 and 5 wt. %, of such polymers are generally required to establish the required viscosity in the mixture for use and thus a correspondingly still higher quantity is required in the oxidizing agent preparation.

Elevated polymer contents, in particular of anionic polymeric thickeners, can, however, lead to problems during the production of the oxidizing agent preparations, since using such high concentrations of thickeners can result in clogging in the production plant and equipment, such as metering pumps and valves, in particular in the event of slight fluctuations in pH value. It is therefore particularly desirable, in addition to ensuring economical use of raw materials, to use agents with a reduced content of polymeric thickeners, providing that the viscosity of the mixture for use is not impaired as a result.

Moreover, good miscibility with coloring, alkalizing and blonding preparations should be ensured.

It is therefore desirable to provide a hydrogen peroxide-containing agent for use in multicomponent color modifying preparations for keratinic fibers, which agent has good miscibility of its sub-components, but has a sufficient viscosity to ensure, on the one hand, that the ready-to-use color modifying preparation can be readily applied and, on the other hand, that it remains where it is intended to act during use and does not run off the fibers. Finally, the agent should be distinguished in that the quantity of polymeric thickener is reduced, such that the above-described problems during production of the agent can be minimized or eliminated.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An agent, including in a cosmetically suitable carrier at least hydrogen peroxide, at least one homo- or copolymer of acrylic acid and/or methacrylic acid and at least one polyurethane, characterized in that the polyurethane is a polycondensation product of polyethylene glycol(s), diisocyanate(s) and optionally ethoxylated fatty alcohol(s).

A method for modifying the color of keratinic fibers, in particular human hair, comprising a plurality of method steps: a) producing a preparation for modifying the color of keratinic fibers immediately prior to use by mixing at least one agent according to any one of claims 1 to 6 and at least one alkalizing preparation, including in a cosmetically suitable carrier at least one alkalizing agent and additionally (i) at least one fatty alcohol and/or (ii) at least one anionic, amphoteric and/or zwitterionic surfactant and/or (iii) at least one amino acid and/or (iv) at least one ethoxylated fatty alcohol and/or (v) at least one cationic and/or amphoteric polymer; b) applying the ready-to-use preparation from method step i) onto the keratin fibers to be treated and leaving the preparation on the fibers for a period of exposure of 5 to 60 minutes; and c) rinsing the fibers.

A multicomponent packaging unit (kit of parts) for modifying the color of keratinic fibers, in particular human hair, comprising at least two components packaged separately from one another, characterized in that the first component is an agent as set forth above and in that the second component is an alkalizing preparation as set forth above.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now unforeseeably been found that an increase in the viscosity of a ready-to-use color modifying preparation can be achieved by combinations of thickening polymers in oxidative preparations for use in color-modifying agents for keratinic fibers, in particular human hair, which, in addition to an anionic polymeric thickener, additionally include a specific polyurethane. This makes it possible to reduce the input quantity of anionic polymeric thickener without there being any need to accept negative effects on the viscosity of the ready-to-use color modifying preparation.

The present invention accordingly firstly provides an agent which includes in a cosmetically suitable carrier at least hydrogen peroxide, at least one homo- or copolymer of acrylic acid and/or methacrylic acid and at least one polyurethane, which is characterized in that the polyurethane is a polycondensation product of polyethylene glycol(s), diisocyanate(s) and optionally ethoxylated fatty alcohol(s).

According to the invention, keratin-containing or keratinic fibers are taken to mean furs, wool, feathers and in particular human hair. Although the use according to the invention is primarily suitable for coloring and/or lightening keratin-containing fibers, there is no reason in principle why it should not also be used in other fields.

Agents according to the invention include the ingredients in a cosmetically suitable and thus physiologically acceptable carrier. For the purposes of the present application, physiologically acceptable carriers are here in particular aqueous, aqueous-alcoholic and alcoholic carriers. For the purposes of the present invention, aqueous-alcoholic carriers should be taken to be hydrous solutions including 3 to 70 wt. % of a $C_1$-$C_4$ alcohol, in particular ethanol or isopropanol, relative to the total weight of the mixture for use. For the purposes of the invention, an aqueous carrier includes at least 30 wt. %, in particular at least 50 wt. % water relative to the total weight of the agent.

The agent according to the invention includes hydrogen peroxide as its first ingredient. Hydrogen peroxide is here used either as a preferably aqueous solution or in the form of a solid addition compound of hydrogen peroxide onto inorganic or organic compounds, such as for example sodium perborate, sodium percarbonate, magnesium percarbonate, sodium percarbamide, polyvinylpyrrolidinone.n $H_2O_2$ (n is a positive integer greater than 0), urea peroxide and melamine peroxide. Agents which are preferred according to the invention include aqueous hydrogen peroxide solutions. The concentration of a hydrogen peroxide solution is determined, on the one hand, by statutory requirements and, on the other hand, by the desired effect.

Agents according to the invention which are particularly preferred are those which include 0.5 to 18 wt. %, preferably 1 to 15 wt. %, particularly preferably 2.5 to 12 wt. % and in particular 3 to 9 wt. % of hydrogen peroxide, relative to the total weight of the agent (calculated as 100% $H_2O_2$).

The agent according to the invention includes as its second essential ingredient at least one polyurethane which is a polycondensation product of polyethylene glycol(s), diisocyanate(s) and optionally ethoxylated fatty alcohol(s).

Due to the fatty alcohol, such polyurethanes according to the invention include at least one fatty chain in their structure and are therefore suitable not only for entering into hydrophilic interactions due to polar structural units, but also for entering into hydrophobic interactions with one another or with further ingredients, and thus for associating.

The polyurethanes according to the invention preferably include at least two hydrophobic fatty chains with 6 to 30, preferably 10 to 24 carbon atoms in the chain, which fatty chains are separated from one another by a hydrophilic structural unit. In the case of two hydrophobic fatty chains, a triblock structure is formed, in which a central, hydrophilic portion is flanked by two lipophilic structural units. Where there are more than two hydrophobic fatty chains in the structure, stellate or grafted structures are, however, also possible.

The hydrophilic structural unit of the polyurethanes obtains its hydrophilic nature substantially thanks to the polyethylene glycol units and optionally the hydrophilic portion of ethoxylated fatty alcohols included therein.

The polyurethanes are in particular polycondensation products of polyethylene glycol with 50 to 1000 ethylene glycol units (PEG-50 to PEG-1000), preferably 50 to 250 ethylene glycol units (PEG-50 to PEG-250).

Diisocyanates which are suitable in the polycondensation products are in particular hexamethylene diisocyanate (HDI), dicyclohexylmethane 4,4'-diisocyanate (SMDI), isophorone diisocyanate (IPDI), 4,4'-methylene bis(phenylisocyanate) (MDI) and diisocyanatotoluene (TDI). Hexamethylene diisocyanate is preferred.

Ultimately, the polyurethanes according to the invention originate from polycondensation with optionally ethoxylated fatty alcohols.

The fatty alcohols are here saturated or unsaturated and linear or branched and in particular include fatty chains of 6 to 30, preferably 10 to 24 carbon atoms in the chain.

Preferred optionally ethoxylated fatty alcohols are here decyl alcohol, lauryl alcohol, myristyl alcohol, cetyl alcohol, palmitoleyl alcohol, stearyl alcohol, oleyl alcohol, elaidyl alcohol, linoleyl alcohol, linolenyl alcohol, eicosyl alcohol, gadoleyl alcohol, arachidonic alcohol, behenyl alcohol, erucyl alcohol, brassidyl alcohol and mixtures thereof.

An example of polyurethanes having a fatty alcohol moiety which is a mixture of lauryl alcohol and myristyl alcohol, is the commercial product Elfacos T210 and an example of polyurethanes having a fatty alcohol moiety which is stearyl alcohol is the commercial product Elfacos T212 or the commercial product Aculyn 46 (stearyl alcohol/PEG-150 to PEG-180/HDI polycondensation product).

One example of a polyurethane with decyl alcohol as the fatty alcohol moiety is the commercial product Aculyn 44 (decyl alcohol/PEG-150 to PEG-180/HDI polycondensation product).

Apart from non-ethoxylated fatty alcohols, it may be preferred to use ethoxylated fatty alcohols. The degree of ethoxylation of the fatty alcohols may here be divided into three different classes, namely low-ethoxylated fatty alcohols with a degree of ethoxylation of 1 to 5 (i.e. 1 to 5 mol of ethylene oxide per mol of fatty alcohol), medium-ethoxylated fatty alcohols with a degree of ethoxylation of 6 to 30 (i.e. 6 to 30 mol of ethylene oxide per mol of fatty alcohol) and high-ethoxylated fatty alcohols with a degree of ethoxylation of above 30 (i.e. >30 mol of ethylene oxide per mol of fatty alcohol).

An example of polyurethanes with high-ethoxylated fatty alcohols is the commercial product Rheolate FX 1100 (Steareth-100/PEG-136/HDI polycondensation product).

Preferred polyurethanes include medium-ethoxylated fatty alcohols with an average degree of ethoxylation of 6 to 30, preferably of 6 to 25. Examples of such ethoxylated fatty alcohols are $C_{12}$-$C_{14}$ Pareth-8, $C_{12}$-$C_{14}$ Pareth-9, $C_{12}$-$C_{14}$ Pareth-10, $C_{12}$-$C_{14}$ Pareth-11, $C_{12}$-$C_{14}$ Pareth-12, $C_{12}$-$C_{14}$ Pareth-14, $C_{12}$-$C_{14}$ Pareth-15, $C_{12}$-$C_{14}$ Pareth-20, $C_{12}$-$C_{14}$ Pareth-25, $C_{16}$-$C_{18}$ Pareth-8, $C_{16}$-$C_{18}$ Pareth-9, $C_{16}$-$C_{18}$ Pareth-10, $C_{16}$-$C_{18}$ Pareth-11, $C_{16}$-$C_{18}$ Pareth-12, $C_{16}$-$C_{18}$ Pareth-14, $C_{16}$-$C_{18}$ Pareth-15, $C_{16}$-$C_{18}$ Pareth-20, $C_{16}$-$C_{18}$ Pareth-25, $C_{18}$-$C_{20}$ Pareth-8, $C_{18}$-$C_{20}$ Pareth-9, $C_{18}$-$C_{20}$ Pareth-10, $C_{18}$-$C_{20}$ Pareth-11, $C_{18}$-$C_{20}$ Pareth-12, $C_{18}$-$C_{20}$ Pareth-14, $C_{18}$-$C_{20}$ Pareth-15, $C_{18}$-$C_{20}$ Pareth-20 and $C_{18}$-$C_{20}$ Pareth-25.

The fatty alcohol component incorporated by condensation into the polyurethane may here be a mixture of fatty alcohols of differing chain lengths and, independently thereof, of a differing average degree of ethoxylation.

One embodiment of the first subject matter of the invention is an agent which is characterized in that it includes as polyurethane a polycondensation product of polyethylene glycol with 50 to 250 ethylene glycol units (PEG-50 to PEG-250), a diisocyanate and ethoxylated $C_{12}$-$C_{20}$ fatty alcohols with a degree of ethoxylation of 6 to 25.

A polyurethane which is particularly preferred is that with the INCI name Polyurethane-39 which is a polycondensation product of PEG-140, hexamethylene diisocyanate and of a mixture of $C_{12}$-$C_{14}$ Pareth-10, $C_{16}$-$C_{18}$ Pareth-11 and $C_{18}$-$C_{20}$ Pareth-11, and which is distributed for example by BASF SE under the trade name Luvigel Star.

A preferred embodiment of the first subject matter of the invention is therefore an agent which is characterized in that the polyurethane is a polycondensation product of PEG-140, hexamethylene diisocyanate (HDI) and of a mixture of $C_{12}$-$C_{14}$ Pareth-10, $C_{16}$-$C_{18}$ Pareth-11 and $C_{18}$-$C_{20}$ Pareth-11.

Thanks to the advantageous polymer combination according to the invention, the agent according to the invention can include the polyurethane in a small quantities, preferably of at most 5 wt. %, while simultaneously exhibiting good thickening properties.

A further embodiment of the first subject matter of the invention is therefore an agent which is characterized in that the polyurethane is present in a proportion by weight of 0.01 to 5 wt. %, preferably 0.05 to 3.0 wt. % and in particular of 0.1 to 2.5 wt. %, in each case relative to the total weight of the agent.

The agent of the first subject matter of the invention includes as its third essential ingredient at least one homo- or copolymer of acrylic acid and/or methacrylic acid. Since the agent for stabilizing the hydrogen peroxide conventionally has an acidic pH value, but the mixture for use has an alkaline pH value, the homo- or copolymer of acrylic acid and/or methacrylic acid undergoes a change in pH value which deprotonates the carboxylic acid groups of acrylic acid or methacrylic acid units and said ionization brings about gelation and thus an increase in viscosity.

In addition to acrylic acid and methacrylic acid, further examples of anionic monomers of which the polymeric anionic thickeners may consist are crotonic acid, itaconic acid, maleic anhydride and 2-acrylamido-2-methylpropanesulfonic acid. In this case, the acidic groups may be present wholly or in part as a sodium, potassium, ammonium, mono- or triethanolammonium salt.

Uncrosslinked and crosslinked polyacrylic acids are preferred homopolymers. In this case, allyl ethers of pentaerythritol, of sucrose and of propylene glycol may be preferred crosslinking agents. Such compounds are commercially available for example under the trademark Carbopol®.

Within this first embodiment, it may furthermore be preferred to use copolymers of at least one anionic monomer, selected from acrylic acid and/or methacrylic acid, and at least one nonionogenic monomer. Preferred nonionogenic monomers are acrylamide, methacrylamide, acrylic acid esters, methacrylic acid esters, itaconic acid mono- and diesters, vinylpyrrolidinone, vinyl ethers and vinyl esters.

The oxidizing agent preparation according to the invention may additionally include at least one anionic acrylic acid and/or methacrylic acid polymer or copolymer.

Preferred polymers of this kind are:
polymers for example of at least 10 wt. % acrylic acid lower alkyl esters, 25 to 70 wt. % methacrylic acid and optionally up to 40 wt. % of a further comonomer,
copolymers of 50 to 75 wt. % ethyl acrylate, 25 to 35 wt. % acrylic acid and 0 to 25 wt. % of other comonomers. Suitable dispersions of this kind are commercially available, for example, under the trade name Latekoll® D (BASF).
copolymers of 50 to 60 wt. % ethyl acrylate, 30 to 40 wt. % methacrylic acid and 5 to 15 wt. % acrylic acid, crosslinked with ethylene glycol dimethacrylate.

Copolymers of acrylic acid, methacrylic acid or the $C_1$-$C_6$ alkyl esters thereof and the esters of an ethylenically unsaturated acid and an alkoxylated fatty alcohol are, however, also preferred. Suitable ethylenically unsaturated acids are in particular acrylic acid, methacrylic acid and itaconic acid; suitable alkoxylated fatty alcohols are in particular Steareth-20 or Ceteth-20. Such copolymers are distributed by Rohm & Haas under the trade name Aculyn® 22 and by National Starch under the trade names Structure® 2001 and Structure® 3001.

Particularly preferred copolymers are for example copolymers of acrylic acid, methacrylic acid or the $C_1$-$C_6$ alkyl esters thereof, as they are distributed under the INCI declaration Acrylates Copolymers. The combination of methacrylic acid and ethyl acrylate and optionally crosslinking, multifunctional monomers is preferred here. One such preferred commercial product is for example Aculyn® 33 or 33A from Rohm & Haas.

One embodiment of the first subject matter of the invention is therefore an agent which is characterized in that it includes at least one copolymer of ethyl acrylate and methacrylic acid and/or acrylic acid as the homo- and/or copolymer of acrylic acid and/or methacrylic acid.

Thanks to the polymer combination according to the invention, the proportion of homo- or copolymer in the agent according to the invention may be kept low, preferably below 2 wt. %, without negative effects on the viscosity in use of the color modifying preparation.

One embodiment of the first subject matter of the invention is therefore an agent which is characterized in that the homo- and/or copolymer(s) of acrylic acid and/or methacrylic acid is present in a proportion by weight of 0.001 to 2.0 wt. %, preferably 0.005 to 1.0 wt. % and in particular of 0.01 to 0.5 wt. %, in each case relative to the total weight of the agent.

It has furthermore proved advantageous for the agent to include at least one stabilizer or complexing agent. Particularly preferred stabilizers are phenacetin, alkali metal benzoates (sodium benzoate) and salicylic acid.

It is also preferred according to the invention to use "complexing agents". Complexing agents are substances which are capable of complexing metal ions. Preferred complexing agents are "chelate complexing agents". Conventional chelate complexing agents which are preferred for the purposes of the present invention are for example polyoxycarboxylic acids, polyamines, ethylenediaminetetraacetic acid (EDTA), ethylenediaminedisuccinic acid (EDDS), nitrilotriacetic acid (NTA) and hydroxyethanediphosphonic acids or the alkali metal salts thereof. Complex-forming polymers, thus polymers which, either in the main chain itself or laterally thereto, bear functional groups which are capable of acting as ligands and react with suitable metal atoms, generally resulting in the formation of chelate complexes, may also be used according to the invention. The polymer-bound ligands of the resultant metal complexes may here originate from just one macromolecule or alternatively belong to different polymer chains. Complexing agents which are preferred according to the invention are polycarboxylic acids, in particular EDTA, and phosphonates, preferably hydroxyalkane- or aminoalkane-phosphonates and in particular 1-hydroxyethane-1,1-diphosphonate (HEDP) or the di- or tetrasodium salt thereof and/or ethylenediaminetetramethylenephosphonate (EDTMP) or the hexasodium salt thereof and/or diethylenetriaminepentamethylenephosphonate (DTPMP) or the hepta- or octasodium salt thereof.

In order to provide further stabilization of the hydrogen peroxide and so improve storage life, the agents according to the invention preferably have an acidic pH value, preferably between pH 2 and pH 5, particularly preferably between pH 3.5 and pH 4.5. A person skilled in the art is familiar with acidifying and alkalizing agents conventional in cosmetics as pH adjusting agents for adjusting the pH value. Alkalizing agents which are usable for adjusting the pH value are typically selected from inorganic salts, in particular of alkali metals and alkaline earth metals, organic alkalizing agents, in particular amines, basic amino acids and alkanolamines, and ammonia. Acidifying agents which are preferred according to the invention are edible acids, such as for example citric acid, acetic acid, malic acid or tartaric acid, together with dilute mineral acids.

The agents according to the invention of the first subject matter of the invention are mixed with a further preparation to form the ready-to-use color modifying preparation. This ready-to-use color modifying preparation has an alkaline pH value, preferably a pH value in the range from 8 to 12 in order to activate the hydrogen peroxide and likewise to swell the keratinic fibers and so facilitate penetration of the active substances. The pH values for the purposes of the present invention are pH values which were measured at a temperature of 22° C.

The mixed preparation therefore preferably includes at least one alkalizing agent in order to compensate the acidic pH value of the agent of the first subject matter of the invention.

It has furthermore proved advantageous for the mixed preparation additionally to include
(i) at least one fatty alcohol and/or
(ii) at least one anionic, amphoteric and/or zwitterionic surfactant and/or
(iii) at least one amino acid and/or
(iv) at least one ethoxylated fatty alcohol and/or
(v) at least one cationic and/or amphoteric polymer.

The present application accordingly also provides a preparation for modifying the color of keratinic fibers, in particular human hair, which is characterized in that the preparation is produced immediately prior to use by mixing at least one agent of the first subject matter of the invention and at least one alkalizing preparation including in a cosmetically suitable carrier at least one alkalizing agent and additionally
(i) at least one fatty alcohol and/or
(ii) at least one anionic, amphoteric and/or zwitterionic surfactant and/or
(iii) at least one amino acid and/or
(iv) at least one ethoxylated fatty alcohol and/or
(v) at least one cationic and/or amphoteric polymer.

The alkalizing agents of the alkalizing preparation are typically selected from inorganic salts, in particular of alkali metals and alkaline earth metals, organic alkalizing agents, in particular amines, basic amino acids and alkanolamines, and ammonia.

Organic alkalizing agents which may be used according to the invention are preferably selected from alkanolamines prepared from primary, secondary or tertiary amines with a $C_2$-$C_6$ alkyl parent substance which bears at least one hydroxyl group. Alkanolamines which are preferred according to the invention are selected from the group triethanolamine, 2-aminoethan-1-ol (monoethanolamine), 2-amino-2-methylpropan-1-ol and 2-amino-2-methylpropane-1,3-diol. One alkanolamine which is particularly preferred is monoethanolamine. Suitable basic amino acids are for example lysine, arginine and ornithine. Inorganic alkalizing agents according to the invention are preferably selected from the group formed of sodium hydroxide, potassium hydroxide, calcium hydroxide, barium hydroxide, sodium phosphate, potassium phosphate, sodium silicate, sodium metasilicate, potassium silicate, ammonium carbonate, sodium carbonate and potassium carbonate.

In one embodiment, the alkalizing preparation additionally includes at least one fatty alcohol. Fatty alcohols for the purposes of the present application are here saturated or unsaturated and linear or branched primary alcohols which in particular include fatty chains of 6 to 30, preferably 10 to 24 carbon atoms in the chain.

Preferred linear fatty alcohols are here decyl alcohol, lauryl alcohol, myristyl alcohol, cetyl alcohol, palmitoleyl alcohol, stearyl alcohol, oleyl alcohol, elaidyl alcohol, linoleyl alcohol, linolenyl alcohol, eicosyl alcohol, gadoleyl alcohol, arachidonic alcohol, behenyl alcohol, erucyl alcohol, brassidyl alcohol and the mixtures thereof which are optionally obtained during industrial production or isolation, such as cetearyl alcohol, coco fatty alcohol or tallow fatty alcohol.

Branched fatty alcohols are also preferred for the purposes of the present invention. Branched fatty alcohols which are usable according to the invention include in particular "Guerbet" alcohols which are obtainable from primary alcohols by the Guerbet reaction. Examples such Guerbet alcohols are (2-)ethylhexyl alcohol, (2-)octyldodecyl alcohol or (2-)hexyldecyl alcohol.

The alkalizing preparation according to the invention preferably includes fatty alcohols in a proportion of 0.5 to 20 wt. %, preferably 1 to 15 wt. %, in particular 1.5 to 12 wt. %, in each case relative to the total weight of the alkalizing preparation.

In a further embodiment, the alkalizing preparation preferably additionally includes at least one anionic, amphoteric and/or zwitterionic surfactant.

Anionic surfactants for the purposes of the invention are any anionic surface-active substances suitable for use on the human body. These are characterized by an anionic water-solubilizing group such as for example a carboxylate, sulfate, sulfonate or phosphate group and a lipophilic alkyl group with approx. 8 to 30 C atoms. The molecule may additionally include glycol or polyglycol ether groups, ester, ether and amide groups and hydroxyl groups. Examples of suitable anionic surfactants are, in each case in the form of sodium, potassium and ammonium and the mono-, di- and trialkanolammonium salts with 2 to 4 C atoms in the alkanol group, linear and branched fatty acids with 8 to 30 C atoms (soaps); ether carboxylic acids, in particular of the formula R—O—$(CH_2$—$CH_2O)_x$—$CH_2$—COOH, in which R is a linear alkyl group having 8 to 30 C atoms and x=0 or 1 to 16; acyl sarcosides; acyl taurides; acyl isethionates; sulfosuccinic acid mono- and -dialkyl esters and sulfosuccinic acid monoalkyl polyoxyethyl esters; linear alkane sulfonates; linear α-olefin sulfonates; sulfonates of unsaturated fatty acids; α-sulfofatty acid methyl esters of fatty acids; alkyl sulfates and alkyl ether sulfates, in particular of formula $RO(CH_2CH_2O)_xSO_3H$, in which R denotes a linear alkyl group with 8 to 30 C atoms and x denotes 0 or a number from 1 to 12; mixtures of surface-active hydroxysulfonates; sulfated hydroxyalkyl polyethylene glycol ethers and/or hydroxyalkylene propylene glycol ethers; esters of tartaric acid and citric acid with alcohols; alkyl and/or alkenyl ether phosphates of formula $RO(C_2H_4O)_x P(=O)(OH)(OR')$, in which R denotes an aliphatic, optionally unsaturated hydrocarbon residue with 8 to 30 carbon atoms, R' denotes hydrogen, a residue $(CH_2CH_2O)_y R$ and x and y mutually independently denote a number from 1 to 10; sulfated fatty acid alkylene glycol esters of formula $RC(O)O(alkO)_n SO_3H$, in which R denotes a linear or branched, aliphatic, saturated and/or unsaturated alkyl residue with 6 to 22 C atoms, alk denotes $CH_2CH_2$, $CHCH_3CH_2$ and/or $CH_2CHCH_3$ and n denotes a number from 0.5 to 5; and monoglyceride sulfates and monoglyceride ether sulfates. Anionic surfactants which are preferred according to the invention are soaps, alkyl sulfates, alkyl ether sulfates and ether carboxylic acids.

Zwitterionic surfactants are those surface-active compounds which bear at least one quaternary ammonium group and at least one carboxylate, sulfonate or sulfate group per molecule. Examples of such zwitterionic surfactants are "betaines" such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 C atoms in the alkyl or acyl group and cocoacylaminoethylhydroxyethylcarboxymethyl glycinate. One preferred zwitterionic surfactant is the fatty acid amide derivative known by the INCI name Cocamidopropyl Betaine.

Amphoteric surfactants are taken to mean those surface-active compounds which, in addition to a $C_8$-$C_{24}$ alkyl or acyl group, include at least one free amino group and at least one —COOH or —$SO_3H$ group per molecule and are capable of forming internal salts. Conventional amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids with in each case approx. 8 to 24 C atoms in the alkyl group. Examples of amphoteric surfactants are N-cocoalkyl aminopropionate, cocoacylaminoethyl aminopropionate, $C_{12}$-$C_{18}$ acyl sarcosine and in particular the surfactant known by the INCI name Disodium Cocoamphodipropionate.

Anionic, amphoteric and/or zwitterionic surfactants which are preferred according to the invention are here selected from Sodium Laureth Sulfate, Sodium Lauryl Sulfate, Sodium Myreth Sulfate, Sodium Cetearyl Sulfate, Sodium Ceteareth Sulfate, Potassium Oleate, Potassium Isostearate, Potassium Myristate, Sodium Laureth-6 Carboxylate, Cocamidopropyl Betaine Disodium Cocoamphodipropionate and mixtures thereof.

The alkalizing preparation according to the invention preferably includes anionic, amphoteric and/or zwitterionic surfactants in a total proportion of 0.1 to 8.0 wt. %, preferably 0.2 to 5.0 wt. %, in particular 0.5 to 3.0 wt. %, in each case relative to the total weight of the alkalizing preparation.

In a further embodiment, the alkalizing preparation preferably additionally includes at least one amino acid.

An amino acid for the purposes of the invention is deemed to be an organic compound which includes in its structure at least one protonatable amino group and at least one —COOH or —$SO_3H$ group. Preferred amino acids are aminocarboxylic acids, in particular α-(alpha)-aminocarboxylic acids and ω-aminocarboxylic acids, wherein α-aminocarboxylic acids are particularly preferred.

α-Aminocarboxylic acids conventionally include at least one asymmetric carbon atom. For the purposes of the present invention, both possible enantiomers may equally well be used as a specific compound or also mixtures thereof, in particular as racemates. It is, however, particularly advantageous to use the preferentially naturally occurring isomeric form, conventionally in L-configuration.

Amino acids which are preferred according to the invention are arginine, serine, lysine, glycine, tyrosine, proline, glutamine, cysteine and histidine and mixtures thereof; arginine, serine, and/or glycine are particularly preferred.

The amino acids may preferably be added to the alkalizing preparations according to the invention in free form. In a range of cases, however, it is also advantageous to use the amino acids in salt form. Preferred salts are in particular hydrochlorides, hydrobromides and sulfates.

The amino acid(s) and/or the salts thereof is/are preferably present in the alkalizing preparations in quantities of 0.1 to 5 wt. %, in particular of 0.5 to 3 wt. %, relative to the total weight of the alkalizing preparation.

In a further embodiment, the alkalizing preparation preferably additionally includes at least one ethoxylated fatty alcohol. The fatty alcohols are here preferably saturated or unsaturated and linear or branched and in particular include fatty chains of 6 to 30, preferably 10 to 24 carbon atoms in the chain.

Preferred ethoxylated fatty alcohols are here selected from ethoxylated, linear fatty alcohols, preferably of a chain length with 8 to 22 carbon atoms. For the purposes of the invention, an ethoxylated fatty alcohol is taken to be an addition product of ethylene oxide onto a fatty alcohol, wherein the degree of ethoxylation indicates the molar quantity of ethylene oxide (EO) which was on average added per mol of fatty alcohol.

Preferred ethoxylated fatty alcohols are ethylene oxide addition products onto capric alcohol, decyl alcohol, lauryl alcohol, isotridecyl alcohol, myristyl alcohol, cetyl alcohol, palmoleyl alcohol, stearyl alcohol, oleyl alcohol, elaidyl alcohol, petroselinyl alcohol, linolyl alcohol, linolenyl alcohol, eleostearyl alcohol, eicosyl alcohol, arachyl alcohol, gadoleyl alcohol, behenyl alcohol, erucyl alcohol and brassidyl alcohol and the technical mixtures thereof, which are obtained, for example, on high pressure hydrogenation of technical methyl esters based on fats and oils or aldehydes from Roelen's oxo synthesis and as the monomer fraction on dimerization of unsaturated fatty alcohols. Particularly preferred addition products are those onto technical fatty alcohols or mixtures thereof with 12 to 18 carbon atoms such as for example coco, palm, palm kernel or tallow fatty alcohol, in particular coco and/or tallow fatty alcohol.

Depending on the manufacturing method, the ethoxylated fatty alcohols according to the invention are obtained as a mixture with a differing distribution of the degree of ethoxylation. For the purposes of the invention, these emulsifiers are therefore characterized by their average degree of ethoxylation which can conventionally be identified from a number following the fatty alcohol suffix "eth-" in the INCI name.

Depending on the average degree of ethoxylation, the ethoxylated fatty alcohols may here be divided into three different classes, namely low-ethoxylated fatty alcohols with a degree of ethoxylation of 1 to 5 (i.e. 1 to 5 mol of ethylene oxide per mol of fatty alcohol), medium-ethoxylated fatty alcohols with a degree of ethoxylation of 6 to 30 (i.e. 6 to 30 mol of ethylene oxide per mol of fatty alcohol) and high-ethoxylated fatty alcohols with a degree of ethoxylation of above 30 (i.e. >30 mol of ethylene oxide per mol of fatty alcohol).

Preferred ethoxylated fatty alcohols with a low average degree of ethoxylation are for example the commercial products Laureth-2 (Dehydrol LS 2, Arlypon FT 90, BASF), Ceteareth-2 (Lowenol C 279, Lowenstein), Ceteth-2 (Nikkol BC 2, Nikko Chemicals), Steareth-2 (Lipocol S 2, Lipo Chemicals), Laureth-3 (Marlipal 24 30, Sasol), Ceteareth-3 (Hostacerin T 3, Clariant), Laureth-4 (Emulgen 104 P, KAO; Nikkol BL 4.2, Nikko Chemicals).

Preferred ethoxylated fatty alcohols with a medium average degree of ethoxylation are for example the commercial products Ceteareth-6 (Eumulgin CS6, Company BASF), Laureth-7 (Marlipal 24 70, Sasol), Ceteth-7 (Nikkol BC 7, Nikko Chemicals), Laureth-9 (Marlipal 24 90, Sasol; Nikkol BL 9, Nikko Chemicals), Laureth-10 Ceteareth-12 (Eumulgin B 1, Cognis), Ceteareth-13 (Emulgen 220, KAO), Ceteth-15 (Nikkol BC 15 TX, Nikko Chemicals Co., Ltd.), Laneth-15 (Polychol 15, Croda), Ceteareth-15 (Eumulgin CS 15, Cognis); Laneth-16 (and) Ceteth-16 (and) Oleth-16 (and) Steareth-16 (as mixture distributed under the trade name Solulan 16, Noveon); Oleth-20 (Ritoleth 20, Rita Corp.), Ceteth-20 (Brij 58 SP, Uniqema; Lipocol C 20, Lipo Chemicals Inc.), Ceteareth-20 (Surfac JH 200, Surfachem; Eumulgin B 2, Cognis), Laneth-20 (Polychol 20, Croda), Steareth-21 (Brij 721 P, Uniqema; Eumulgin S 21, Cognis); Ceteareth-23 (Mergital C 23, Cognis), Laureth-23 (Canasol BJ 35, Canamax); Ceteareth-25 (Cremophor A 25, BASF); Ceteareth-27 (Plurafac A 38, BASF); Ceteareth-30 (Lipocol SC 30, Lipo Chemicals; Eumulgin B 3, Cognis).

Preferred ethoxylated fatty alcohols with a high average degree of ethoxylation are for example the commercial products: Ceteth-40 (Nikkol BC 40 TX, Nikko Chemicals Co., Ltd.), Laneth-40 (Polychol 40, Croda), Oeth-50 (Nikkol BO 50 V, Nikko Chemicals Co., Ltd.), Ceteareth-50 (Genapol T 500, Clariant; Mergital CS 50, Cognis), Ceteareth-60 (Findet 1618 A 72, KAO Corp.), Ceteareth-80 (Lutensol AT 80, BASF), Ceteth-150 (Nildcol BC 150, Nikko Chemicals), Ceteareth-50 is particularly preferred.

Ethoxylated fatty alcohols which are particularly preferred according to the invention are selected from Ceteareth-12, Ceteareth-20, Ceteareth-30 and/or Ceteareth-50.

The alkalizing preparations preferably include ethoxylated fatty alcohols in a proportion of 0.1 to 10 wt. %, in particular of 0.2 to 5 wt. %, relative to the total weight of the alkalizing preparation.

In a further embodiment, the alkalizing preparation preferably additionally includes at least one amphoteric and/or cationic polymer.

Cationic and/or amphoteric polymers should be taken to be those polymers which include at least one quaternary nitrogen atom, for example in the form of an ammonium group. Suitable cationic and/or amphoteric polymers are for example quaternized cellulose derivatives, as are commercially available under the names Celquat and Polymer JR, preferably Celquat H 100, Celquat L 200 and Polymer JR 400;

copolymers of vinylpyrrolidinone with quaternized derivatives of dialkylaminoacrylate and dialkylaminomethacrylate, such as for example vinylpyrrolidinone-dimethylaminomethacrylate copolymers quaternized with diethyl sulfate, which are commercially available under the names Gafquat 734 and Gafquat 755 (INCI name Polyquaternium-11);

vinylpyrrolidone-methoimidazolinium chloride copolymers, as are offered for sale under the name Luviquat;

quaternized polyvinyl alcohol, quaternized urea- or urethane-including polymers, such as polymers with the INCI name Polyquaternium-2 or Polyquaternium-27, quaternized amide-containing polymers, such as polymers with the INCI name Polyquaternium-17 or Polyquaternium-18 and homo- or copolymers of diallyldimethylammonium chloride.

A cationic and/or amphoteric polymer which is preferred according to the invention is at least a homo- or copolymer of diallyldimethylammonium chloride.

Anionic or nonionic monomers, such as for example acrylic acid, methacrylic acid, alkyl esters of acrylic acid or of methacrylic acid, acrylamide, vinylimidazole, vinylpyrrolidinone or vinyl acetate, may preferably additionally be used in the diallyldimethylammonium chloride copolymers.

In one particularly preferred embodiment, the homo- or copolymer of diallyldimethylammonium chloride is selected from diallyldimethylammonium chloride homopolymer (trade name Merquat 100; Polyquaternium-6), diallyldimethylammonium chloride-acrylamide copolymer (trade name Merquat 550; Polyquaternium-7), diallyldimethylammonium chloride-acrylic acid copolymer (trade name Merquat 280 or Merquat 281; Polyquaternium-22), diallyldimethylammonium chloride-acrylamide-acrylic acid copolymer (trade name Merquat Plus 3330; Polyquaternium-39) and/or diallyldimethylammonium chloride-vinylimidazole-vinylpyrrolidinone copolymer (trade name Luviquat Sensation; Polyquaternium-87).

In a further preferred embodiment, the cationic and/or amphoteric polymer is a homo- or copolymer of esters or amides of acrylic or methacrylic acid as monomers which bear a cationic charge in the ester or amide side chain.

Examples of such monomers are acrylamidopropyltrimonium chloride, N,N-dimethyl-N-1-[3-(2-methyl-1-oxo-2-propenyl)amino]propyl]-1-dodecanaminium chloride (methacrylamidopropyldodecyldimonium chloride), 2-(trimethylammonio)ethyl methacrylate chloride, N,N,N-trimethyl-N-3-(2-methyl-1-oxo-2-propenyl)amino]-1-propanaminium chloride (methacrylamidopropyltrimonium chloride) and 2-(N,N-dimethyl-N-ethylammonio)ethyl methacrylate ethylsulfate.

In one particularly preferred embodiment, the homo- or copolymer of esters or amides of acrylic or methacrylic acid is selected from Polyquaternium-11 (trade name Gafquat 440, Gafquat 734, Gafquat 755, Luviquat PQ-11 PN), Polyquaternium-28 (trade name Gafquat HS 100), Polyquaternium-37 (trade name Synthalen), Polyquaternium-55 (trade name Styleze W 20/W 10), Polyquaternium-69 (trade name Aquastyle 200) or Acrylamidopropyltrimonium Chloride/Acrylates Copolymer (trade name Product W 37194).

In one particularly preferred embodiment, the alkalizing agent includes at least one cationic and/or amphoteric polymer selected from Polyquaternium-2, Polyquaternium-4, Polyquaternium-6, Polyquaternium-7, Polyquaternium-10, Polyquaternium-11, Polyquaternium-16, Polyquaternium-18, Polyquaternium-22, Polyquaternium-24, Polyquaternium-28, Polyquaternium-32, Polyquaternium-37, Polyquaternium-39, Polyquaternium-44, Polyquaternium-46, Polyquaternium-55, Polyquaternium-59, Polyquaternium-67, Polyquaternium-68, Polyquaternium-69, Polyquaternium-72, Polyquaternium-87, Acrylamidopropyltrimonium Chloride/Acrylates Copolymer, and mixtures thereof.

It is preferred for the cationic and/or amphoteric polymer to be present in the alkalizing preparation according to the invention in a proportion of 0.1 to 5 wt. %, preferably 0.2 to 3 wt. %, in each case relative to the total weight of the alkalizing preparation.

In one particularly preferred embodiment, the alkalizing preparation additionally includes at least one fatty alcohol and furthermore at least one anionic and/or zwitterionic and/or amphoteric surfactant and/or at least one amphoteric and/or cationic polymer and/or at least one ethoxylated fatty alcohol and/or at least one amino acid.

In one particularly preferred embodiment, the alkalizing preparation additionally includes at least one anionic and/or zwitterionic and/or amphoteric surfactant and furthermore at least one fatty alcohol and/or at least one amphoteric and/or cationic polymer and/or at least one ethoxylated fatty alcohol and/or at least one amino acid.

In one particularly preferred embodiment, the alkalizing preparation additionally includes at least one amphoteric and/or cationic polymer and furthermore at least one anionic and/or zwitterionic and/or amphoteric surfactant and/or at least one fatty alcohol and/or at least one ethoxylated fatty alcohol and/or at least one amino acid.

In one particularly preferred embodiment, the alkalizing preparation additionally includes at least one ethoxylated fatty alcohol and furthermore at least one anionic and/or zwitterionic and/or amphoteric surfactant and/or at least one amphoteric and/or cationic polymer and/or at least one fatty alcohol and/or at least one amino acid.

In one particularly preferred embodiment, the alkalizing preparation additionally includes at least one amino acid and furthermore at least one anionic and/or zwitterionic and/or amphoteric surfactant and/or at least one amphoteric and/or cationic polymer and/or at least one ethoxylated fatty alcohol and/or at least one fatty alcohol.

Particularly preferred alkalizing preparations are those which additionally include at least one fatty alcohol and at least one anionic surfactant and at least one amphoteric polymer and at least one ethoxylated fatty alcohol and at least one amino acid.

Particularly preferred alkalizing preparations are those which additionally include at least one fatty alcohol and at least one zwitterionic surfactant and at least one amphoteric polymer and at least one ethoxylated fatty alcohol and at least one amino acid.

Particularly preferred alkalizing preparations are those which additionally include at least one fatty alcohol and at least one amphoteric surfactant and at least one amphoteric polymer and at least one ethoxylated fatty alcohol and at least one amino acid.

Particularly preferred alkalizing preparations are those which additionally include at least one fatty alcohol and at least one anionic surfactant and at least one cationic polymer and at least one ethoxylated fatty alcohol and at least one amino acid.

Particularly preferred alkalizing preparations are those which additionally include at least one fatty alcohol and at least one zwitterionic surfactant and at least one cationic polymer and at least one ethoxylated fatty alcohol and at least one amino acid.

Particularly preferred alkalizing preparations are those which additionally include at least one fatty alcohol and at least one amphoteric surfactant and at least one cationic polymer and at least one ethoxylated fatty alcohol and at least one amino acid.

The preparation for modifying the color of keratinic fibers is here produced in a specific weight or volume ratio from an agent of the first subject matter of the invention and at least one alkalizing preparation. Preferred color modifying preparations are those in which the weight ratio of hydrogen peroxide-containing agent of the first subject matter of the invention and alkalizing preparation is a ratio of 4:1 to 1:4, preferably 2:1 to 1:2.

In one embodiment of the second subject matter of the invention, the preparation for modifying the color of keratinic fibers is an oxidation coloring agent.

In this case, the alkalizing preparation additionally includes at least one oxidation dye precursor as color-modifying component.

One embodiment of the second subject matter of the invention is therefore a preparation for modifying the color of keratinic fibers which is characterized in that the alkalizing preparation additionally includes at least one oxidation dye precursor.

The oxidation dye precursor present is preferably is at least one oxidation dye precursor of the developer type (developer component), preferably in combination with at least one oxidation dye precursor of the coupler type (coupler component).

Preferred oxidation dye precursors of the developer type are p-phenylenediamine derivatives. Preferred p-phenylenediamines are selected from one or more compounds of the group which is formed from p-phenylenediamine, p-tolylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(2-hydroxyethyl)-p-phenylenediamine, 4-N,N-bis-(2-hydroxyethyl)amino-2-methylaniline, 4-N,N-bis-(2-hydroxyethyl)amino-2-chloroaniline, 2-(2-hydroxyethyl)-p- phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxane and the physiologically acceptable salts thereof. p-Phenylenediamine derivatives which are particularly preferred according to the invention are selected from at least one compound of the group p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, 2-methoxymethyl-p-phenylenediamine and the physiologically acceptable salts thereof.

It may furthermore be preferred according to the invention to use compounds which include at least two aromatic nuclei which are substituted with amino and/or hydroxyl groups as the developer component. Preferred binuclear developer components are selected in particular from at least one of the following compounds: N,N'-bis-(2-hydroxyethyl)-N,N'-bis-(4'-aminophenyl)-1,3-diaminopropan-2-ol, N,N'-bis-(2-hydroxyethyl)-N,N'-bis-(4'-aminophenyl)ethylenediamine, N,N'-bis-(4'-aminophenyl)tetramethylenediamine, N,N'-bis-(2-hydroxyethyl)-N,N'-bis-(4'-amino-phenyltetramethylenediamine, N,N'-bis-(4-(methylamino)phenyl)tetramethylenediamine, N,N'-diethyl-N,N'-bis-(4'-amino-3'-methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl)piperazine, N-(4'-aminophenyl)-p-phenylenediamine and 1,10-bis-(2',5'-diaminophenyl)-1,4,7,10-tetraoxadecane and the physiologically acceptable salts thereof. Particularly preferred binuclear developer components are selected from N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane or one of the physiologically acceptable salts thereof.

It may furthermore be preferred according to the invention to use a p-aminophenol derivative or one of the physiologically acceptable salts thereof as the developer component. Preferred p-aminophenols are in particular p-aminophenol, N-methyl-p-aminophenol, 4-amino-3-methylphenol, 4-amino-3-fluorophenyl, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenyl, 4-amino-2-chlorophenol, 4-amino-2,6-dichlorophenyl, 4-amino-2-(diethylaminomethyl)phenol and the physiologically acceptable salts thereof. Particularly preferred compounds are p-aminophenol, 4-amino-3-methylphenol, 4-amino-2-aminomethylphenol, 4-amino-2-(1,2-dihydroxyethyl)phenol and 4-amino-2-(diethylaminomethyl)phenol.

The developer component may furthermore be selected from o-aminophenol and the derivatives thereof, such as for example 2-amino-4-methylphenol, 2-amino-5-methylphenol or 2-amino-4-chlorophenol.

The developer component may furthermore be selected from heterocyclic developer components, such as for example from pyrimidine derivatives, pyrazole derivatives, pyrazolopyrimidine and pyrazolopyrazole derivatives or the physiologically acceptable salts thereof. Preferred pyrimidine derivatives are in particular the compounds 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine. Preferred pyrazole derivatives are in particular the compounds selected from 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t.-butyl-1-methylpyrazole, 4,5-diamino-1-t.-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, and the physiologically acceptable salts thereof, but in particular 4,5-diamino-1-(2-hydroxyethyl)pyrazole. Preferred pyrazolopyrimidines are the compounds which are selected from pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 3-amino-7-dimethylamino-2,5-dimethylpyrazolo[1,5-a]pyrimidine and the physiologically acceptable salts thereof and the tautomeric forms thereof, if a tautomeric equilibrium exists. A preferred pyrazolopyrazole derivative is 2,3-diamino-6,7-dihydro-1H,5H-pyrazoles[1,2-a]pyrazol-1-one.

Particularly preferred developer components are selected from at least one compound from the group, which is formed from p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4'-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)-phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and the physiologically acceptable salts thereof. Particularly preferred developer components are p-tolylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and the physiologically acceptable salts thereof.

The developer components are preferably used in a quantity of 0.0001 to 2.5 wt. %, preferably 0.001 to 1.5 wt. %, in each case relative to the ready-to-use preparation.

In the context of oxidative coloring, coupler components alone do not form any significant coloring effect, but instead always require the presence of developer components. It is therefore preferred according to the invention that, when at least one coupler component is used, at least one developer component is additionally used.

Coupler components according to the invention are preferably selected as at least one compound from one of the following classes: m-aminophenol, o-aminophenol, m-diaminobenzene, o-diaminobenzene and/or the derivatives thereof; naphthalene derivatives with at least one hydroxyl group; di- or trihydroxybenzene; pyridine derivatives; pyrimidine derivatives; specific indole derivatives and indoline derivatives; pyrazolone derivatives (for example 1-phenyl-3-methylpyrazol-5-one); morpholine derivatives (for example 6-hydroxybenzomorpholine or 6-aminobenzomorpholine); quinoxaline derivatives (for example 6-methyl-1,2,3,4-tetrahydroquinoxaline), and mixtures of two or more compounds from one or more of these classes.

Preferred m-aminophenol coupler components are selected from at least one compound from the group formed by 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol and the physiologically acceptable salts thereof.

Preferred m-diaminobenzene coupler components are selected from at least one compound from the group formed by m-phenylenediamine, 2-(2,4-diaminophenoxy)ethanol, 1,3-bis-(2,4-diaminophenoxy)propane, 1-methoxy-2-amino-4-(2'-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)-ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene and the physiologically acceptable salts thereof.

Preferred o-diaminobenzene coupler components are selected from at least one compound from the group which is formed by 3,4-diaminobenzoic acid and 2,3-diamino-1-methylbenzene and the physiologically acceptable salts thereof.

Preferred naphthalene derivatives with at least one hydroxyl group are selected from at least one compound of the group formed by 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene, Preferred di- or trihydroxybenzenes and the derivatives thereof are selected from at least one compound of the group formed by resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene.

Preferred pyridine derivatives are selected from at least one compound of the group formed by 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and the physiologically acceptable salts thereof.

Preferred pyrimidine derivatives are selected from at least one compound of the group formed by 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and the physiologically acceptable salts thereof.

Preferred indole derivatives are selected from at least one compound of the group formed by 4-hydroxyindole, 6-hydroxyindole and 7-hydroxyindole and the physiologically acceptable salts thereof.

Preferred indoline derivatives are selected from at least one compound of the group formed by 4-hydroxyindoline, 6-hydroxyindoline and 7-hydroxyindoline and the physiologically acceptable salts thereof.

Coupler components which are particularly preferred according to the invention are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxy-ethyl)amino]-4,5-dimethylphenyl}amino)ethanol, 2-[3-morpholin-4-ylphenyl)amino]-ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts thereof. Particularly preferred are: resorcinol, 2-methylresorcinol, 5-amino-2-methylphenol, 3-aminophenol, 2-(2,4-diaminophenoxy)ethanol, 1,3-bis-(2,4-diaminophenoxy)propane, 1-methoxy-2-amino-4-(2'-hydroxyethylamino)benzene, 2-amino-3-hydroxypyridine, and 1-naphthol and one of the physiologically acceptable salts thereof.

The coupler components are preferably used in a quantity of 0.0001 to 2.5 wt. %, preferably 0.001 to 1.0 wt. %, in each case relative to the ready-to-use preparation.

Developer components and coupler components are generally used in approximately molar quantities relative to one another. While molar use has also proven convenient, a certain excess of individual oxidation dye precursors is not disadvantageous, such that developer components and coupler components may be present in a molar ratio of 1:0.5 to 1:3, in particular 1:1 to 1:2.

At least one substantive dye may furthermore additionally be present as color-imparting component. These are dyes which key directly to the hair and do not need an oxidative process to develop the color. Substantive dyes may be subdivided into anionic, cationic and nonionic substantive dyes. Substantive dyes are conventionally nitrophenylenediamines, nitroaminophenols, azo dyes, anthraquinones or indophenols. The substantive dyes are in each case preferably used in a quantity of 0.0001 to 2.0 wt. %, preferably of 0.001 to 1.0 wt. %, in each case relative to the total preparation for use.

Preferred anionic substantive dyes are the compounds known by the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue. Preferred cationic substantive dyes are cationic triphenylmethane dyes, such as Basic Blue 7, Basic Blue 26, Basic Violet 2 and Basic Violet 14, aromatic systems which are substituted with a quaternary nitrogen group, such as for example Basic Yellow 57, Basic Red 76, Basic Blue 99, HC Blue 16 (Bluequat B), Basic Blue 347, Basic Brown 16 and Basic Brown 17, and substantive dyes which include a heterocycle which comprises at least one quaternary nitrogen atom, in particular Basic Yellow 87, Basic Orange 31 and Basic Red 51. The cationic substantive dyes which are distributed under the trademark Arianor® are likewise preferred cationic substantive dyes according to the invention. Suitable nonionic substantive dyes are in particular nonionic nitro and quinone dyes and neutral azo dyes. Preferred nonionic substantive dyes are the compounds known by the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenol)amino]-benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol. Dye combinations which are preferred according to the invention are those which include at least the combination of tetrabromophenol blue and Acid Red 92; tetrabromophenol blue and Acid Red 98; tetrabromophenol blue and Acid Red 94; tetrabromophenol blue and Acid Red 87 or tetrabromophenol blue and Acid Red 51.

Finally, additional bleach boosters which enhance the action of the hydrogen peroxide of the agent of the first subject matter of the invention may be used as a color-modifying component in lightening agents.

In one embodiment, the alkalizing preparation according to the invention therefore includes an additional bleach booster as a color-modifying component. Additional bleach boosters which may be used for the purposes of the present invention are peroxo compounds and furthermore compounds which, under perhydrolysis conditions, give rise to aliphatic peroxocarboxylic acids and/or substituted perbenzoic acid, carbonic acid derivatives, in particular carbonate salts or hydrogencarbonate salts of ammonium, alkali metals or alkaline earth metals, alkyl carbonates, alkyl carbamates, silyl carbonates and silyl carbamates.

The bleach booster is preferably selected from ammonium peroxodisulfate, alkali metal peroxodisulfates, ammonium peroxomonosulfate, alkali metal hydrogenperoxomonosulfates, alkali metal peroxodiphosphates and alkaline earth metal peroxides. Particularly preferred bleach boosters are ammonium peroxodisulfate, potassium peroxodisulfate, sodium peroxodisulfate, potassium hydrogenperoxomonosulfate, potassium peroxodiphosphate, magnesium peroxide and barium peroxide. Agents which are particularly preferred according to the invention are those which include at least one inorganic salt, selected from peroxomonosulfates and/or peroxodisulfates, as bleach booster. It has further been found in the work leading to the present invention to be particularly preferable for the agents according to the invention to include at least two different peroxodisulfates. Preferred peroxodisulfate salts are here combinations of ammonium peroxodisulfate and potassium peroxodisulfate and/or sodium peroxodisulfate. The peroxo compounds are present in a quantity of 0.1 to 25 wt. %, in particular in a quantity of 0.5 to 15 wt. %, relative to the total weight of the ready-to-use agent.

The persulfate salts or peroxodisulfate salts are generally used in anhydrous form and in the form of an optionally dedusted powder, a paste or in the form of a pressed molding.

In a further, preferred embodiment the color modifying preparation may include at least one cationic pyridinium derivative as bleach booster. Preferred compounds are 4-acylpyridinium derivatives and 2-acylpyridinium derivatives. In particular, the following are preferred: 2-acetyl-1-methylpyridinium p-toluenesulfonate and 4-acetyl-1-methylpyridinium p-toluenesulfonate. Preferred cationic pyridinium derivatives are furthermore here cationic 3,4-dihydroisoquinolinium derivatives, in particular N-methyl-3,4-dihydroisoquinolinium p-toluenesulfonate.

The bleach boosters used in addition to or instead of peroxo compounds are preferably present in the cosmetic preparations according to the invention in quantities of 0.05 to 10 wt. %, in particular in quantities of 0.2 to 5 wt. %, in each case relative to the total weight of the ready-to-use color modifying preparation.

At least one optionally hydrated $SiO_2$ compound may additionally be added as a bleach booster to increase further the lightening power of the composition according to the invention. Although even small quantities of the optionally hydrated $SiO_2$ compounds increase lightening power, it may be preferred according to the invention to use the optionally hydrated $SiO_2$ compounds in quantities of 0.05 wt. % to 15 wt. %, particularly preferably in quantities of 0.15 wt. % to 10 wt. % and particularly preferably in quantities of 0.2 wt. % to 5 wt. %, in each case relative to the anhydrous composition according to the invention. The stated quantities here in each case indicate the content of $SiO_2$ compounds (excluding their water content) in the agents. Preferred optionally hydrated $SiO_2$ compounds are silicas, the oligomers and polymers and the salts thereof. The optionally hydrated $SiO_2$ compounds may be present in various forms. According to the invention, the $SiO_2$ compounds are preferably used in the form of silica gels or particularly preferably as water glass. Water glasses formed of a silicate of the formula $(SiO_2)_n(Na_2O)_m(K_2O)_p$, wherein n denotes a positive rational number and m and p mutually independently denote a positive rational number or 0, providing that at least one of the parameters m or p differs from 0 and the ratio between n and the sum of m and p is between 1:4 and 4:1, are preferred according to the invention. Metasilicates, which according to the above formula are distinguished by having a ratio between n and the sum of m and p of <1 and may be considered to be chain-like polymeric structures of the anion $[SiO_3]^{2-}$, may in particular preferably be used. Sodium metasilicate of formula $[NaSiO_3]_x$ is here particularly preferred.

Ready-to-use preparations according to the invention are preferably aqueous, flowable preparations. The color modifying preparations according to the invention may furthermore include any active substances, additives and auxiliary substances known for such preparations.

The ready-to-use color modifying preparations as a mixture of alkalizing preparation and hydrogen peroxide-containing agent may here include further surface-active substances selected from nonionic and cationic surfactants.

Nonionic surfactants and emulsifiers include as hydrophilic group for example a polyol group, a polyalkylene glycol ether group or a combination of a polyol group and polyglycol ether group. Such compounds are for example, in addition to the ethoxylated fatty alcohols which have already been described, the addition products of 1 to 50 mol of ethylene oxide and/or 0 to 5 mol of propylene oxide onto linear and branched fatty alcohols with 8 to 30 C atoms, onto fatty acids with 8 to 30 C atoms and onto alkylphenols with 8 to 15 C atoms in the alkyl group; addition products end group-terminated with a methyl residue or $C_2$-$C_6$ of 1 to 50 mol of ethylene oxide and/or 0 to 5 mol of propylene oxide onto linear and branched fatty alcohols with 8 to 30 C atoms, onto fatty acids with 8 to 30 C atoms and onto alkylphenols with 8 to 15 C atoms in the alkyl group, such as for example the grades obtainable under the commercial names Dehydrol LS, Dehydrol PS (Cognis); polyglycerol esters and alkoxylated polyglycerol esters, such as for example poly(3)glycerol diisostearate (commercial product: Lameform TGI (Henkel)) and poly(2)glycerol polyhydroxystearate (commercial product: Dehymuls PGPH (Henkel)); polyol fatty acid esters, such as for example the commercial product Hydagen HSP (Cognis) or Sovermol grades (Cognis); higher alkoxylated, propoxylated and in particular ethoxylated, mono-, di- and triglycerides with a degree of alkoxylation of greater than 5, such as for example glycerol monolaurate+20 ethylene oxide and glycerol monostearate+20 ethylene oxide; amine oxides; hydroxy mixed ethers; sorbitan fatty acid esters and addition products of ethylene oxide onto sorbitan fatty acid esters such as for example polysorbates and sorbitan monolaurate+20 mol ethylene oxide (EO); sugar fatty acid esters and addition products of ethylene oxide onto sugar fatty acid esters; addition products of ethylene oxide onto fatty acid alkanolamides and fatty amines; fatty acid N-alkylglucamides; alkylphenols and alkylphenol alkoxylates with 6 to 21, in particular 6 to 15, carbon atoms in the alkyl chain and 5 to 30 ethylene oxide and/or propylene oxide units; alkyl polyglycosides corresponding to the general formula RO—$(Z)_x$, wherein R denotes alkyl, Z denotes sugar and x denotes the number of sugar units.

Nonionic emulsifiers for the purposes of the invention furthermore include the polymerization products of ethylene oxide and propylene oxide on saturated or unsaturated fatty acid esters of polyhydric alcohols with saturated or unsaturated fatty acids; alkyl esters of saturated or unsaturated fatty acids or alkylphenols and the alkoxylates thereof; in particular ethylene glycol ethers of fatty alcohols; mixed ethylene and propylene glycol ethers with fatty alcohols; fatty acid esters on sorbitan and polyethylene glycol; esters of non-hydroxylated $C_6$-$C_{30}$ alkyl monocarboxylic acids with polyethylene glycol; and addition products of alkylphenols onto ethylene oxide and/or propylene oxide.

Cationic surfactants of the quaternary ammonium compound, ester quat and amidoamine type are preferred according to the invention in ready-to-use preparations. Preferred quaternary ammonium compounds are ammonium halides, in particular chlorides and bromides, such as alkyltrimethylammonium chlorides, dialkyldimethylammonium chlorides and trialkylmethylammonium chlorides, and the imidazolinium compounds known under the INCI names Quaternium-27 and Quaternium-83. Quaternized protein hydrolysates are further cationic surfactants which are usable according to the invention. Alkylamidoamines are conventionally produced by amidating natural or synthetic fatty acids and fatty acid cuts with dialkylaminoamines such as stearamidopropyl dimethylamine. Ester quats, which are likewise preferred, are quaternized ester salts of fatty acids with triethanolamine, quaternized ester salts of fatty acids with diethanolalkylamines and quaternized ester salts of fatty acids with 1,2-dihydroxypropyldialkylamines. Such products are distributed, for example, under the trademarks Stepantex, Dehyquart and Armocare. The products Armocare VGH-70, an N,N-bis(2-palmitoyloxyethyl)dimethylammonium chloride, and Dehyquart F-75, Dehyquart C-4046, Dehyquart L80 and Dehyquart AU-35 are examples of such ester quats.

The surfactants are preferably present in the color modifying preparations used according to the invention in quantities of 0.05 to 25 wt. %, relative to the entire color modifying preparation. Quantities of 0.1 to 15 wt. %, in particular of 1 to 10 wt. %, are particularly preferred.

Further active substances, auxiliary substances and additives which are usable according to the invention are for example nonionic polymers (such as vinylpyrrolidinone/vinyl acrylate copolymers, polyvinylpyrrolidinone and vinylpyrrolidinone/vinyl acetate copolymers, and polysiloxanes); anionic polymers (such as polyacrylic acid, crosslinked polyacrylic acids, vinyl acetate/crotonic acid copolymers, vinylpyrrolidinone/vinyl acrylate copolymers, vinyl acetate/butyl maleate/isobornyl acrylate copolymers, methyl vinyl ether/maleic anhydride copolymers and acrylic acid/ethyl acrylate/N-tert.-butylacrylamide terpolymers; thickeners (such as agar-agar, guar gum, alginates, xanthan gum, gum arabic, karaya gum, locust bean flour, linseed gums, dextrans, cellulose derivatives, for example methylcellulose, hydroxyalkylcellulose and carboxymethylcellulose, starch fractions and derivatives such as amylose, amylopectin and dextrins, clays such as for example bentonite or completely synthetic hydrocolloids such as for example polyvinyl alcohol); structuring agents (such as sugar, maleic acid and lactic acid) and consistency providers (such as sugar esters, polyol esters or polyol alkyl ethers); protein hydrolysates, in particular elastin, collagen, keratin, milk protein, soy protein and wheat protein hydrolysates, the condensation products thereof with fatty acids; perfume oils; cyclodextrins; solvents and solubilizing agents (such as ethanol, isopropanol, ethylene glycol, propylene glycol, glycerol, dimethyl isosorbide and diethylene glycol); defoamers such as silicones; dyes and pigments for coloring the agent; antidandruff active ingredients (such as piroctone olamine, zinc omadine and climbazole); light stabilizers (in particular derivatized benzophenones, cinnamic acid derivatives and triazines); active substances (such as allantoin, pyrrolidonecarboxylic acids, cholesterol and the salts thereof); further fats and waxes (such as beeswax, montan wax and paraffins); swelling and penetrating substances (such as glycerol, propylene glycol monoethyl ether, carbonates, hydrogencarbonates, guanidines, ureas and primary, secondary and tertiary phosphates); opacifiers (such as latex, styrene/PVP and styrene/acrylamide copolymers); pearlescent agents (such as ethylene glycol mono- and distearate as well as PEG-3 distearate); propellants (such as propane/butane mixtures, $N_2O$, dimethyl ether, $CO_2$ and air) together with antioxidants.

A person skilled in the art will select these further substances in accordance with the desired properties of the agents. With regard to further optional components and the quantities of these components used, reference is explicitly made to the relevant handbooks known to a person skilled in the art, for example Kh. Schräder, Grundlagen and Rezepturen der Kosmetika, 2nd edition, Hüthig Buch Verlag, Heidelberg, 1989.

The color modifying preparations according to the invention have a viscosity which permits easy application and distribution on the fibers to be treated, but simultaneously ensures that the preparation remains where it is desired to act during the period of use. The color modifying preparations thus have good viscosities in use and are distinguished by having a reduced content of polymeric thickeners.

The color modifying preparations according to the invention preferably therefore have a viscosity of 5 to 50 Pa·s, preferably of 10 to 20 Pa·s. In order to ensure better comparability of the measurement results, the viscosities stated within this application were in each case determined using a Brookfield DV-II+Pro viscometer with spindle #5 at 4 rpm (revolutions per minute) at RT (22° C.) in 590 ml beakers, tall form.

The color modifying preparation is produced immediately prior to use by mixing the hydrogen peroxide-containing agent of the first subject matter of the invention and the alkalizing preparation. Immediately here means a period of a few seconds to at most 10 min. The agent is then applied for use onto the keratinic fibers, in particular human hair.

The invention accordingly further provides a method for modifying the color of keratinic fibers, in particular human hair, which method comprises a plurality of method steps:
i) producing a preparation for modifying the color of keratinic fibers immediately prior to use by mixing at least one agent of the first subject matter of the invention and at least one alkalizing preparation, containing in a cosmetically suitable carrier at least one alkalizing agent and additionally
　(i) at least one fatty alcohol and/or
　(ii) at least one anionic, amphoteric and/or zwitterionic surfactant and/or
　(iii) at least one amino acid and/or
　(iv) at least one ethoxylated fatty alcohol and/or
　(v) at least one cationic and/or amphoteric polymer;
ii) applying the ready-to-use preparation from method step i) onto the keratin fibers to be treated and leaving the preparation on the fibers for a period of exposure of 5 to 60 minutes;
iii) rinsing the fibers.

One particular advantage of the method according to the invention is that, thanks to the polymer combination of the hydrogen peroxide-containing agent, distinctly less effort and time is required to obtain a homogeneous mixture for use.

This may for example be quantified in that, once an agent of the first subject matter of the invention and an alkalizing preparation have been combined in the product-specific quantity ratio in suitable sales packaging materials, such as a bottle, mixing is performed. Mixing conventionally proceeds by shaking the reclosed bottle. During shaking, the required number of "shakes/knocks" of the bottle is counted, wherein significantly fewer shakes are required in order to obtain a homogeneous mixture for the color modifying agent according to the invention than for conventional commercial comparison products.

A further advantage of the method according to the invention is that, thanks to the polymer combination of the hydrogen peroxide-containing agent, improved dispensing of the mixture for use from the application bottle is possible.

To this end, the number of times the bottle had to be knocked in order to dispense the mixture for use from the bottle in which mixing was performed, through the application tip in a similar manner to customer use was documented. It was found that significantly less effort is required to dispense the mixture for use of color modifying agents according to the invention than for conventional commercial comparison products, such that use is considerably simplified for the user.

In the case of an oxidation dyeing agent, the preferred period of exposure is 5 to 40 min, preferably 10 to 30 min. In the case of lightening or bleaching color modifying agents (lightening or blonding agents), the preferred period of exposure is 30 to 60 min, preferably 40 to 60 min.

Use temperatures may be in a range between 15 and 40° C. After the period of exposure, the color modifying agent is removed from the hair by rinsing. Rewashing with a shampoo is not required if a carrier with an elevated surfactant content has been used.

The statements made above apply mutatis mutandis to this subject matter of the invention.

In order to avoid lack of stability during storage of the individual agents prior to use, while at the same time providing the user with the individual components together, it is convenient to package the preparations separately and offer them for sale in an outer packaging.

The invention accordingly further provides a multicomponent packaging unit (kit of parts) for modifying the color of keratinic fibers, in particular human hair, comprising at least two components packaged separately from one another, characterized in that
the first container includes an agent of the first subject matter of the invention and the second container includes an alkalizing preparation including in a cosmetically suitable carrier at least one alkalizing agent and at least one fatty alcohol.

The preparations of the multicomponent packaging unit are provided in two containers which are packaged separately from one another. For the purposes of the present invention, a container is taken to mean a package assuming the form of an optionally reclosable bottle, a tube, a can, a small pouch, a sachet or similar packages. The invention does not place any limits on the material of the package. The packages are, however, preferably made of glass or plastics material.

According to the invention, it may be advantageous for the multicomponent packaging unit according to the invention to include at least one further hair treatment agent, in particular a conditioning agent, in a separate container. The packaging unit may furthermore include application aids, such as combs, brushes or paintbrushes, personal protective clothing, in particular disposable gloves, and optionally a set of instructions.

In order to improve mixing, it is advantageous for the container which includes an agent of the first subject matter of the invention to have a reclosable orifice, such as for example a snap or screw closure. This facilitates addition of the alkalizing agent from the second container, which in turn is preferably in the form of a small pouch or sachet in the case of anhydrous, in particular pulverulent color modifying agents, or in the form of a tube in the case of flowable color modifying agents.

With regard to the further preferred embodiments of the multicomponent packaging unit, the above explanations regarding the preceding subjects of the invention apply mutatis mutandis.

Thanks to the combination of polymeric thickeners in the hydrogen peroxide-containing agents, the input quantity of polymeric thickener in the color modifying preparations can advantageously be reduced. As a consequence, it is possible, on the one hand, to reduce use of raw materials and, on the other hand, to minimize the problems caused in the production process by an elevated quantity of thickener.

Finally, the applicational characteristics of the color modifying preparations are improved in comparison with conventional commercial products.

The present invention accordingly also provides the use of a hydrogen peroxide-containing agent of the first subject matter of the invention for improving the applicational characteristics of a preparation for modifying the color of keratinic fibers.

The improved applicational characteristics are here on the one hand the easier miscibility of the agent of the first subject matter of the invention with the alkalizing preparation and thus faster, more efficient and user friendlier production of a homogeneous preparation for modifying the color of keratinic fibers, in particular human hair.

On the other hand, the improved applicational characteristics are manifested in improved dispensing of the ready-to-use preparation for modifying the color of keratinic fibers.

Finally, the use of a hydrogen peroxide-containing agent of the first subject matter of the invention makes it possible to reduce the polymer content while achieving constant or improved viscosities of the ready-to-use color modifying preparation.

The statements made above apply mutatis mutandis to this subject matter of the invention.

EXAMPLES

1) Dye creams—alkalizing preparations (quantities stated in wt. %)

| Raw materials | F1 | F2 | F3 | F4 |
|---|---|---|---|---|
| Cetearyl Alcohol | 6.60 | 6.60 | 11.00 | 8.70 |
| Ethanolamine | — | — | 6.97 | 5.47 |
| Ammonium Hydroxide | 3.34 | 3.34 | — | — |
| Coconut Alcohol | 2.40 | 2.40 | 5.40 | 4.02 |
| Ammonium Chloride | — | — | 3.00 | — |
| Sodium Laureth-6 Carboxylate | 2.10 | 2.10 | — | — |
| Sodium Myreth Sulfate | 1.96 | 1.96 | — | — |
| Sodium Laureth Sulfate | — | — | 0.81 | 0.81 |
| Disodium Cocoamphodipropionate | — | — | 0.80 | 0.80 |
| Cocamidopropyl Betaine | — | — | 0.61 | 0.61 |
| Serine | 1.00 | — | — | — |
| Arginine | — | — | 1.00 | 1.00 |
| Ammonium Sulfate | 0.93 | 0.29 | — | 2.00 |
| Acrylamidopropyltrimonium Chloride/Acrylates Copolymer | 0.74 | 0.73 | — | — |
| Polyquaternium-22 | — | — | 0.62 | 0.62 |
| Xanthan | — | — | 0.18 | 0.13 |
| Coco-Glucoside | 0.67 | 0.67 | — | — |
| Ceteareth-12 | 0.60 | 0.60 | — | — |
| Ceteareth-20 | 0.60 | 0.60 | 0.45 | 0.34 |
| Ceteareth-30 | — | — | 0.45 | 0.33 |
| Ceteareth-50 | — | — | 1.80 | 1.34 |
| Glyceryl Oleate | 0.56 | 0.56 | 0.20 | — |
| Sodium Sulfite | 0.40 | 0.40 | — | 0.20 |
| Sodium Silicate | 0.19 | 0.19 | 0.19 | 0.19 |
| Etidronic Acid | 0.12 | 0.12 | 0.12 | 0.12 |
| Ascorbic Acid | 0.10 | 0.10 | — | — |
| Citric Acid | 0.10 | 0.10 | 0.10 | 0.10 |
| Sodium Hydroxide | 0.10 | — | — | — |
| Sodium Chloride | 0.05 | 0.05 | 0.11 | 0.11 |
| Propylene Glycol | — | — | 0.90 | 0.67 |
| Toluene-2,5-Diamine Sulfate | 0.11 | 1.18 | 3.00 | 0.84 |
| 1,3-Bis-(2,4-Diaminophenoxy) Propane HCl | — | 0.44 | 0.244 | — |
| 2,7-Naphthalenediol | — | 0.29 | — | — |
| 4-Chlororesorcinol | 0.03 | — | — | — |
| Resorcinol | 0.03 | 1.66 | 0.87 | 0.52 |
| 2-Methylresorcinol | 0.01 | — | — | 0.02 |
| 3-Aminophenol | 0.002 | — | 0.47 | 0.24 |
| 6-Methoxy-2-Methylamino-3-Aminopyridine HCl | — | — | 0.15 | — |
| 4-Amino-3-methylphenol | — | — | — | 0.67 |
| 5-Amino-2-methylphenol | — | — | — | 0.23 |
| 2-Amino-6-chloro-4-nitrophenol | — | — | — | 0.18 |
| 2-Amino-3-hydroxypyridine | — | — | — | 0.14 |
| 1-Naphthol | — | — | — | 0.05 |
| 4-Amino-3-nitrophenol | — | — | — | 0.05 |
| Perfume | q.s. | q.s. | q.s. | q.s. |
| Aqua | | Ad 100 | | |

The fatty base was melted together at 80° C. and dispersed with some of the water. The remaining ingredients of the formulation were then stirred in succession. The formulation was made up to 100 wt. % with water and the formulation stirred until cold.

2) Hydrogen peroxide-containing agent (quantities stated in wt. %)

| Raw material | Comparison 1 | Invention 1 | Comparison 2 | Invention 2 |
|---|---|---|---|---|
| Potassium hydroxide | 0.12 | 0.12 | — | — |
| Sodium hydroxide | — | — | 0.33 | 0.33 |
| 2,6-Dicarboxypyridine | 0.10 | 0.10 | 0.10 | 0.10 |
| Disodium pyrophosphate | 0.03 | 0.03 | 0.03 | 0.03 |
| Etidronic Acid | 0.15 | 0.15 | 0.90 | 0.90 |
| Sodium Laureth Sulfate | 0.54 | 0.33 | 0.54 | 0.54 |
| Luvigel Star | — | 10.00 | — | 0.85 |
| Aculyn 33A | 15.00 | 1.20 | 2.50 | 0.11 |
| Hydrogen peroxide | 5.93 | 5.93 | 7.42 | 7.42 |
| Water, deionized | Ad 100 | Ad 100 | Ad 100 | Ad 100 |

Raw materials: Aculyn 33A (approx. 28% active substance; INCI name: Acrylates Copolymer, Aqua; Rohm & Haas); Luvigel Star (approx. 20% active substance; INCI name: Polyurethane-39; BASF).

3) Mixtures for Use:

Dye creams F1 and F2 were in each case combined at room temperature in a 1:1 ratio by weight with agents Invention 1 and Comparison 1 and dye creams F3 and F4 in each case with agents Invention 2 and Comparison 2 and intimately mixed.

The following mixing viscosities were obtained:

| Color modifying preparation | Polymer content* | Mixing viscosity** |
|---|---|---|
| #1 F1 + Comparison 1 (not according to the invention) | 2.1% PAc | 25000 |
| #2 F1 + Invention 1 (according to the invention) | 0.1% PAc + 1.0 PU | 33000 |
| #3 F2 + Comparison 1 (not according to the invention) | 2.1% PAc | 20000 |
| #4 F2 + Invention 1 (according to the invention) | 0.1% PAc + 1.0 PU | 20000 |
| #5 F3 + Comparison 2 (not according to the invention) | 0.35% PAc | 21000 |
| #6 F3 + Invention 2 (according to the invention) | 0.015% PAc + 0.085% PU | 23000 |
| #7 F4 + Comparison 2 (not according to the invention) | 0.35% PAc | 14000 |
| #8 F4 + Invention 2 (according to the invention) | 0.015% PAc + 0.085% PU | 15000 |

*in wt. % of the mixture for use; PAc = Acrylates Copolymer; PU = Polyurethane-39
**in mPa · s, measured with a Brookfield DV-II + Pro viscometer with spindle #5 at 4 rpm at RT (22° C.) in 590 ml beakers, tall form.

The ready-to-use color modifying preparations according to the invention are here distinguished relative to the comparison agents by constant or improved viscosity, despite the significant reduction in the absolute quantity of polymer.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent, comprising in a cosmetically suitable carrier at least hydrogen peroxide, at least one homo- or copolymer of acrylic acid and/or methacrylic acid and at least one polyurethane, characterized in that the polyurethane is a polycondensation product of polyethylene glycol(s), diisocyanate(s) and optionally ethoxylated fatty alcohol(s).

2. The agent according to claim 1, wherein the polyurethane is a polycondensation product of polyethylene glycol with 50 to 250 ethylene glycol units (PEG-50 to PEG-250), a diisocyanate and ethoxylated $C_{12}$-$C_{20}$ fatty alcohols with a degree of ethoxylation of 6 to 25.

3. The agent according to claim 1, wherein the polyurethane is a polycondensation product of PEG-140, hexamethylene diisocyanate and a mixture of $C_{12}$-$C_{14}$ Pareth-10, $C_{16}$-$C_{18}$ Pareth-11 and $C_{18}$-$C_{20}$ Pareth-11.

4. The agent according to claim 1, wherein the agent comprises at least one copolymer of ethyl acrylate and methacrylic acid and/or acrylic acid as the homo- and/or copolymer of acrylic acid and/or methacrylic acid.

5. The agent according to claim 1, wherein the polyurethane is present in a proportion by weight of 0.01 to 5 wt. % relative to the total weight of the agent.

6. The agent according to claim 1, wherein the homo- and/or copolymer(s) of acrylic acid and/or methacrylic acid is/are present in a proportion by weight of 0.001 to 2.0 wt. % relative to the total weight of the agent.

7. A preparation for modifying the color of keratinic fibers, in particular human hair, characterized in that the preparation is produced immediately prior to use by mixing at least one agent according claim 1 and at least one alkalizing preparation comprising in a cosmetically suitable carrier at least one alkalizing agent and additionally
   (i) at least one fatty alcohol and/or
   (ii) at least one anionic, amphoteric and/or zwitterionic surfactant and/or
   (iii) at least one amino acid and/or
   (iv) at least one ethoxylated fatty alcohol and/or
   (v) at least one cationic and/or amphoteric polymer.

8. The preparation according to claim 7, wherein the alkalizing preparation additionally includes at least one oxidation dye precursor.

9. A method for modifying the color of keratinic fibers, in particular human hair, comprising:
   i) producing a preparation for modifying the color of keratinic fibers immediately prior to use by mixing at least one agent according to claim 1 and at least one alkalizing preparation, comprising in a cosmetically suitable carrier at least one alkalizing agent and additionally
      (i) at least one fatty alcohol and/or
      (ii) at least one anionic, amphoteric and/or zwitterionic surfactant and/or
      (iii) at least one amino acid and/or
      (iv) at least one ethoxylated fatty alcohol and/or
      (v) at least one cationic and/or amphoteric polymer;
   ii) applying the ready-to-use preparation from method step i) onto the keratin fibers to be treated and leaving the preparation on the fibers for a period of exposure of 5 to 60 minutes; and
   iii) rinsing the fibers.

10. A multicomponent packaging unit (kit of parts) for modifying the color of keratinic fibers, in particular human hair, comprising at least two components packaged separately from one another, characterized in that
   the first component is an agent according to claim 1 and further characterized in that
   the second component is an alkalizing preparation comprising in a cosmetically suitable carrier at least one alkalizing agent and additionally
   (i) at least one fatty alcohol and/or
   (ii) at least one anionic, amphoteric and/or zwitterionic surfactant and/or
   (iii) at least one amino acid and/or
   (iv) at least one ethoxylated fatty alcohol and/or
   (v) at least one cationic and/or amphoteric polymer.

* * * * *